(12) United States Patent
Kroll et al.

(10) Patent No.: US 8,563,005 B2
(45) Date of Patent: Oct. 22, 2013

(54) ACTINOBACILLUS SUIS ANTIGENS

(75) Inventors: Jeremy Kroll, Urbandale, IA (US); Philip Utley, Slater, IA (US); Dianna Murphy Jordan, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 147 days.

(21) Appl. No.: 12/942,579

(22) Filed: Nov. 9, 2010

(65) Prior Publication Data

US 2011/0123570 A1    May 26, 2011

Related U.S. Application Data

(60) Provisional application No. 61/259,728, filed on Nov. 10, 2009.

(51) Int. Cl.

| | |
|---|---|
| *A61K 39/02* | (2006.01) |
| *A61K 45/00* | (2006.01) |
| *A61K 47/00* | (2006.01) |
| *A01N 63/00* | (2006.01) |
| *C12P 1/04* | (2006.01) |
| *C12P 1/00* | (2006.01) |

(52) U.S. Cl.
USPC .................. 424/234.1; 424/278.1; 424/93.4; 435/41; 435/170

(58) Field of Classification Search
None
See application file for complete search history.

(56) References Cited

FOREIGN PATENT DOCUMENTS

WO    9713523 A1    4/1997

OTHER PUBLICATIONS

Kaur et al., The FASEB Journal, 2010, 24:1-11.*
Emulsigen-D Technical Bullentin 2012.*
Burrows et al., "Molecular Characterization of an RTX Toxin Determinant from *Actinobacillus suis*". Jun. 1992, Infection and Immunity, vol. 60, No. 6, pp. 2166-2173.
Devenish et al., "Humoral Antibody Response and Protective Immunity in Swine following Immunization with the 104-Kilodalton hemolysin of *Actinobacillus pleuropneumoniae*". Dec. 1990, Infection and Immunity, vol. 58, No. 12, pp. 3829-3832.
Fedorka-Cray et al., "Efficacy of a Cell Extract from *Actinobacillus (Haemophilus) pleuropneumoniae* Serotype 1 against Disease in Swine". Feb. 1990, Infection and Immunity, vol. 58, No. 2, pp. 358-365.
Goethe et al., "A novel strategy for protective *Actinobacillus pleuropneumoniae* subunit vaccines: detergent extraction of cultures induced by iron restriction". 2001, Vaccine, vol. 19, pp. 966-975.
Wang et al., "Positive role for rApxIVN in the immune protection of pigs against infection by *Actinobacillus pleuropneumoniae*". 2009, Vaccine, vol. 27, pp. 5816-5821.
International Search Report and Written Opinion of the International Searching Authority for PCT/US2010/055951 mailed Jan. 28, 2011.
Oliveira, S. "Pig Respiratory Bacterial Pathogens: Bacterial Overview and Vaccine Trends". Paradigms in Pig Science, Nottingham University Press, Nottingham, UK, 2007, pp. 169-178.
Oliveira, S, "Update on *Actinobacillus suis* diagnosis, epidemiology, and control: on the path from good to great". American Association of Swine Veterinarians, 2007, pp. 371-376.
Rullo et al., "The structural basis for the serospecificity of *Actinobacillus suis* serogroup O:2". Biochemistry and Cell Biology, vol. 84, No. 2, 2006, pp. 184-190.
Simpson, E.H., "Measurement of Diversity". Nature, vol. 163, Apr. 30, 1949, p. 688.
Slavic et al., "Comparative pathogenicity of different *Actinobacillus suis* O/K serotypes". The Canadian Journal of Veterinary Research, vol. 64, 2000, pp. 81-87.
Slavic et al., "Prevalence of O1/K1- and O2/K3- Reactive *Actinobacillus suis* in Healthy and Diseased Swine". Journal of Clinical Microbiology, vol. 38, No. 10, Oct. 2000, pp. 3759-3762.
Versalovic et al., "Distribution of repetitive DNA sequences in eubacteria and application to fingerprinting of bacterial genomes". Nucleic Acids Research, vol. 19, No. 24, 1991, pp. 6823-6831.

* cited by examiner

*Primary Examiner* — Vanessa L Ford
*Assistant Examiner* — Lakia Tongue
(74) *Attorney, Agent, or Firm* — Michael P. Morris; Wendy M. Gombert

(57) ABSTRACT

The invention provides immunogenic compositions useful for inhibiting, treating, protecting, or preventing infection by *Actinobacillus suis*. These immunogenic compositions are demonstrated to usefully stimulate immunogenic responses in treated pigs. Some vaccines stimulated reactions sufficient to be protective against *A. suis*. In addition, the invention provides kits comprising the immunogenic compositions; as well as, methods of using the compositions and kits.

18 Claims, 1 Drawing Sheet

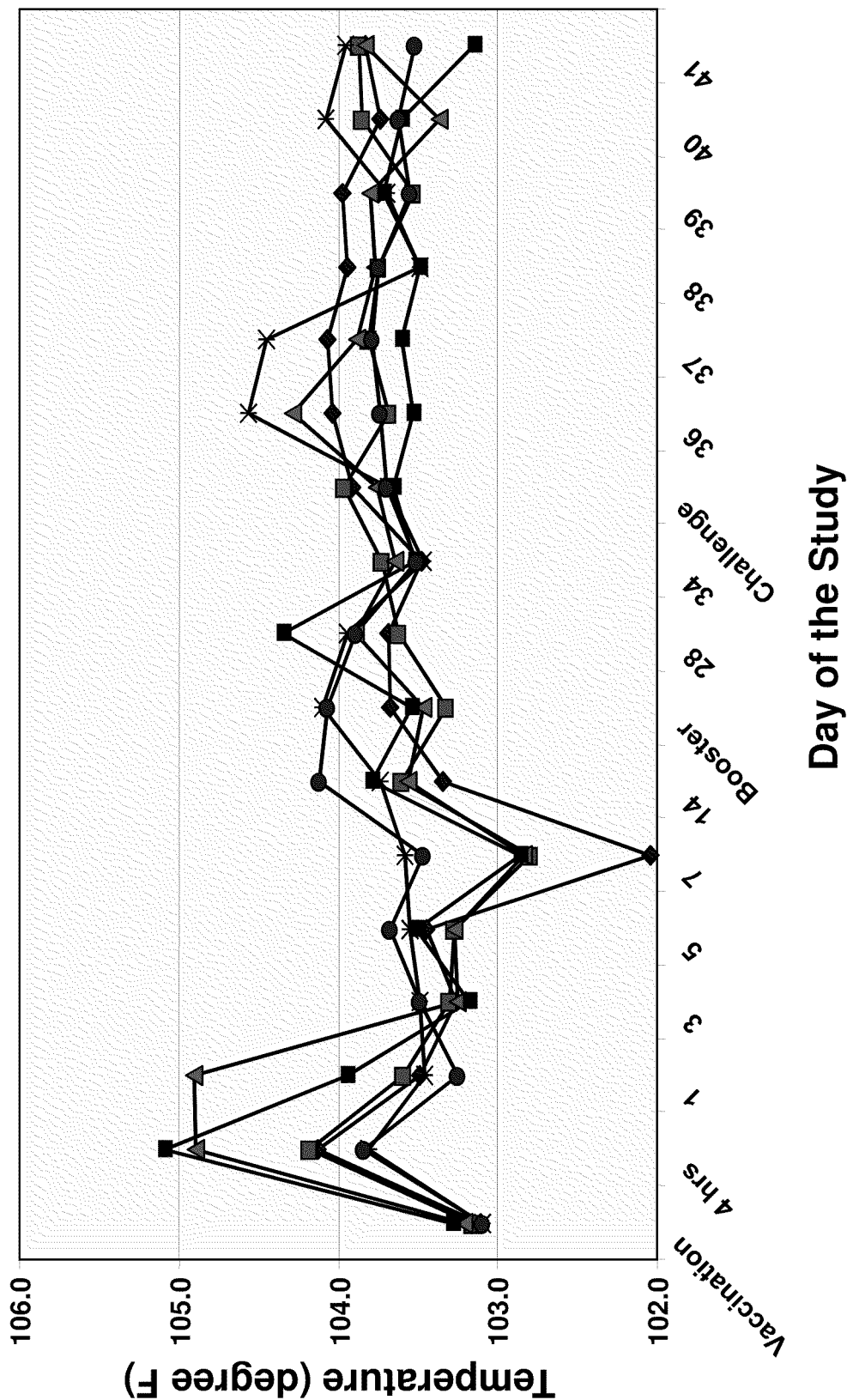

ACTINOBACILLUS SUIS ANTIGENS

RELATED APPLICATIONS

This application relates to and claims priority to U.S. Provisional Patent Application No. 61/259,728, which was filed Nov. 10, 2009. The teachings and contents of which are incorporated herein by reference in their entirety. All applications are commonly owned.

BACKGROUND OF THE INVENTION

A. Field of the Invention

The present invention relates to methods and compositions useful for inhibiting, treating, protecting, or preventing infection by *Actinobacillus suis*.

B. Description of the Related Art

*Actinobacillus suis* has recently emerged as a new threat to the swine industry in the United States. Previously associated with high mortality in "high health" herds, *A. suis* is now recognized as an important pathogen of conventional herds. It is particularly detrimental to younger animals. Infection results in actinobacillosis and can cause sudden death in both neonate and weaned pigs. Symptoms in weaned pigs include anorexia, fever, cyanosis, congestion of the extremities, respiratory distress, pneumonia, necrotizing pneumonia, persistent cough, skin lesions, and fatal septicemia. Pneumonia, arthritis, septicemic signs, pleurisy, pericarditis, and miliary abscesses are known to occur in finishing pigs. Actinobacillosis also causes metritis and abortion in sows.

The gross pathology of actinobacillosis is characterized by lesions found in lungs, kidney, heart, liver, spleen, intestines and skin; hemorrhages and necrosis; and pneumonic lesions resembling pleuropneumonia. Histopathologically, the disease is characterized by the presence of bacterial thromboemboli with accompanying fibrinohemorrhagic necrosis in the vessels of various tissues; necrotizing bronchopneumonia; and pleuritis. Causes and contributing factors to infection include precipitation by Porcine Reproductive and Respiratory Syndrome (PRRS) infection, teeth clipping, de-tailing, scrubbed knees, and entry via either respiration, cuts, or abrasions.

*Actinobacillus suis* is an opportunistic, gram-negative, non-motile, aerobic and facultative anaerobic coccobacillus that colonizes the upper respiratory tract. Genotyping of *A. suis* isolates recovered from clinical cases in the North American swine herds has revealed a limited genetic variability, with only 13 strains being identified among 74 isolates recovered from 29 different herds. The Simpson's diversity index (also known as species diversity index, see Simpson, 1949) for *A. suis* genotypes is 0.64, meaning that a random isolate has a 64% chance of being included in a unique genotype group using for example BOX-PCR (Simpson, 1949; Versalovic et al, 1991; Oliveira et al, 2007). Compared with *H. parasuis*, for example, which has a diversity index of 0.93 (Oliveira et al, 2007), *A. suis* is relatively clonal.

The phenotypic diversity of *A. suis* is also relatively limited. Only 2 serovars, namely O1 and O2 (Rullo, Papp-Szabo and Michael, 2006), and three capsular types, K1-3, have been described so far. Pathogenicity studies suggest that isolates from serogroup O2 tend to be more virulent than O1 isolates (Slavic, DeLay and Hayes, 2000). Serotyping of *A. suis* isolates used for autogenous vaccine production also confirms that a higher percentage of O2 isolates were associated with clinical disease compared with O1 isolates (Slavic, Toffner, and Monteiro, 2000). Although some of the *A. suis* virulence factors are known (e.g. the RTX toxins Apx $I_{var.\ suis}$ and Apx $II_{var.\ suis}$), the factors that may trigger systemic infection still remain to be defined. Some of these potential factors include lipopolysaccharide (LPS) and capsular polysaccharides (CPS), outer membrane protein A (OmpA), proteases, and iron acquisition.

Currently, there are no commercial vaccines available for the control of *A. suis*, and most field veterinarians rely on autogenous vaccines and antimicrobial treatments to control disease. The development of a vaccine that will potentially protect against most isolates in the field is desirable; however, necessary data regarding the association between genotype, serovar, toxin, protein profiles, and factors that are involved in the pathogenesis of *A. suis* infection still remain to be defined. Herein, such data are provided, as well as, vaccines, and their methods of use, against *A. suis*.

SUMMARY OF THE INVENTION

The present invention provides new immunogenic compositions that are useful for protecting a subject against *Actinobacillus suis* infection. These compositions are also useful for inhibiting, treating, or preventing infection by various strains or types of *Actinobacillus suis*.

Compositions of the invention comprise a supernatant collected from one or more *A. suis* cultures grown to between 0.650 $OD_{650}$ and 0.850 $OD_{650}$; and an adjuvant. Preferably the supernatant is inactivated, most preferably by formalin. The supernatant is also preferably filtered, such as through a 45 micron filter. Filtration may occur before or after inactivation as deemed appropriate for a given situation. The supernatant, more preferably the filtered supernatant, is essentially free from *A. suis* cells but may contain multiple cellular components.

The skilled artisan will recognize that any of a variety of adjuvants may be suitably included in a composition of the invention. One exemplary adjuvant is Emulsigen®-D, an oil-in-water emulsion which incorporates dimethyldioctadecylammonium bromide (DDA). The determination of adjuvant will, in part, depend upon the nature of the subject that is to receive the composition; the method of administration to the subject; and conditions under which the composition is to be administered. For example, the adjuvant and supernatant, or filtered supernatant, may be admixed together prior to administration to a subject, administered simultaneously, or administered sequentially to a subject.

Suitable subjects of the immunogenic compositions of the invention include animals and humans. Animals in which the immune response is stimulated by use of compositions or methods of the invention include livestock, such as pigs, calves, chickens, goats, and sheep, and domestic animals, such as mice, rabbits, dogs, cats, and horses. Preferred animals include porcines, murids, equids, lagomorphs, and bovids. Most preferably the animal is a porcine.

The invention also provides methods of provoking an immune response against *Actinobacillus* reducing the incidence of or severity of a clinical sign associated with *Actinobacillus suis* infection in a subject comprising administering to the subject an immunogenic composition of the invention. Clinical signs associated with *A. suis* that may be reduced in incidence or severity in a subject include meningitis, septicemia, metritis, pneumonia, crysipelas-like lesions, and abortion. Any one of which may be lessened by the administration of a composition of the invention relative to a subject not receiving the immunogenic composition. Preferred compositions of the invention elicit a protective immunological response that is at least a 10% reduction in at least one clinical sign of an *A. suis* infection.

A preferred *Actinobacillus suis* infection that may be reduced by administration of a composition of the invention is *A. suis* ISU-8594.

The invention also provides methods of making or preparing immunogenic compositions of the invention that may be useful in the making of a medicament. Such methods include the steps of growing an *Actinobacillus suis* culture to between 0.650 $OD_{650}$ and 0.850 $OD_{650}$; collecting a supernatant from the culture; filtering the supernatant to yield a filtrate; and mixing the filtrate with an adjuvant. Such methods may also include inactivating the supernatant, preferably prior to admixing the supernatant with an adjuvant. Inactivation may occur either before or after filtering the supernatant.

The invention further provides methods of diagnosing an *Actinobacillus suis* infection in a subject. Such methods comprise: a) providing a filtered supernatant prepared by growing an *A. suis* culture to between 0.650 $OD_{650}$ and 0.850 $OD_{650}$, collecting supernatant from the culture, and filtering the supernatant; b) contacting the filtered supernatant with a sample obtained from the subject; and c) identifying the subject as having an *A. suis* infection if an antibody capable of binding a component in the filtered supernatant is detected in the sample.

Those of skill in the art will be familiar with a variety of techniques suitable for ascertaining if an antibody is capable of binding to a component. For example, binding may be detected by using a second antibody capable of binding the antibody in the sample. Binding by such second antibodies may by detected by a colorimetric assay or other suitable means.

The invention also provides kits that comprise: a) a filtered supernatant prepared by growing an *Actinobacillus suis* culture to between 0.650 $OD_{650}$ and 0.850 $OD_{650}$, collecting a supernatant of the culture, and filtering the supernatant; b) an adjuvant; and c) a container for packaging the supernatant and adjuvant. The filtered superantant and adjuvant may be packaged together or separately.

A kit may further comprise instructions for use of the kit. It may also comprise a means of administering the filtered supernatant and adjuvant to a subject. A means of admixing the supernatant and adjuvant together may also be included in a kit.

Compositions of the invention may further comprise a veterinarily acceptable carrier, second adjuvant, or combination thereof. Such compositions may be used as a vaccine and comprise an attenuated vaccine, an inactivated vaccine, or combinations thereof. Such vaccines elicit a protective immunological response against at least one disease associated with *Actinobacillus*.

Preferred inactivation agents for use in methods of the invention are selected from the group consisting of binary ethyleneimine (BEI) and formalin. Formalin is a more preferred inactivation agent. Those of skill in the art will recognize that other inactivation agents and methods (i.e. heating, changing pH, etc.) are known in the art and may be interchangeably used in the practice of the invention, as long as, such agents or deactivation methods do not adversely alter the immunogenic properties or safety of the composition produced.

Methods of the invention may also comprise admixing a composition of the invention with a veterinarily acceptable carrier, adjuvant, or combination thereof. Those of skill in the art will recognize that the choice of carrier, adjuvant, or combination will be determined by the delivery route, personal preference, and animal species among others.

Preferred routes of administration include intranasal, oral, intradermal, and intramuscular. Administration in drinking water, most preferably in a single dose, is preferred. The skilled artisan will recognize that compositions of the invention may also be administered in two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, intrapulmonarily, or intravaginally. Depending on the desired duration and effectiveness of the treatment, the compositions according to the invention may be administered once or several times, also intermittently, for instance on a daily basis for several days, weeks or months and in different dosages.

The invention also provides kits for vaccinating a subject comprising a set of printed instructions; a dispenser capable of administering a vaccine to an animal; and a supernatant from an *A. suis* culture having one or more components that effectively stimulates an immune response in a subject. Kits of the invention may further comprise a veterinarily acceptable carrier, adjuvant, or combination thereof.

A dispenser in a kit of the invention is capable of dispensing its contents as droplets; and the *A. suis* supernatant included in the kit is capable of reducing the severity of at least one clinical sign of an *A. suis* infection when administered to a subject. Preferably, the severity of a clinical sign is reduced by at least 10% as compared to an untreated, infected subject.

An "immunogenic or immunological composition" refers to a composition of matter that comprises at least one *A. suis* supernatant, or immunogenic portion thereof, that elicits an immunological response of a cellular or antibody-mediated immune response to the composition in the subject. In a preferred embodiment of the present invention, an immunogenic composition induces an immune response and, more preferably, confers protective immunity against one or more of the clinical signs of a *Actinobacillus* infection.

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the vaccinated subject will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of clinical symptoms, reduced pathogen persistence, a reduction in the overall pathogen load and/or a reduction of pathogen excretion.

"Protection against *A. suis*", "protective immunity", "functional immunity", and similar phrases, mean an immune response against *A. suis* generated by an immunization schedule that results in fewer deleterious effects than would be expected in a non-immunized subject that has not been previously exposed to *A. suis*. That is, the severity of the deleterious effects of the infection are lessened in an immunized subject because the subject's immune system is resistant to the bacterium. Infection may be reduced, slowed, or possibly fully prevented, in an immunized subject, preferably a pig. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in the subjects, in comparison to wild-type infection. For example, it should refer to any reduction of pathogen load, pathogen shedding, reduction in pathogen transmission, or reduction of any clinical sign symptomatic of A. suis infection. Preferably these clinical signs are reduced in subjects receiving the composition of the present invention by at least 10% in comparison to subjects not receiving the composition and may become infected. More preferably clinical signs are reduced in subjects receiving the composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with *A. suis* infection in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 20%, preferably 30%, more preferably 50%, and even more preferably 70% lower than in the non-vaccinated control group after the challenge with an infectious *Actinobacillus* bacterium.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

Other exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Cabopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

Herein, "effective dose" means, but is not limited to, an amount of *A. suis* supernatant or filtered supernatant that elicits, or is able to elicit, an immune response that yields a reduction of clinical symptoms in a subject to which the supernatent is administered.

"Safety" refers to the absence of adverse consequences in a vaccinated subject following vaccination, including but not limited to: potential reversion of a bacterium-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of a composition of the invention that, when administered to a subject, elicits, or is able to elicit—directly or indirectly—an immune response in the subject against *A. suis*.

Methods for the treatment or prophylaxis of infections caused by *A. suis* are also disclosed. The method comprises administering an effective amount of the immunogenic composition of the present invention to a subject, wherein said treatment or prophylaxis is selected from the group consisting of reducing signs of *A. suis* infection, reducing the severity of or incidence of clinical signs of *A. suis* infection, reducing the mortality of subjects from *A. suis* infection, and combinations thereof.

"Mortality", in the context of the present invention, refers to death caused by *A. suis* infection, and includes the situation where the infection is so severe that an animal is euthanized to prevent suffering and provide a humane ending to their life.

"Attenuation" means reducing the virulence of a pathogen. In the present invention "attenuation" is synonymous with "avirulent". In the present invention, an attenuated bacterium is one in which the virulence has been reduced so that it does not cause clinical signs of an *A. suis* infection but is capable of inducing an immune response in the target subject, but may also mean that the clinical signs are reduced in incidence or severity in subjects infected with the attenuated *A. suis* in comparison with a "control group" of subjects infected with non-attenuated *A. suis* and not receiving the attenuated bacterium. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above.

An "effective amount" for purposes of the present invention, means an amount of an immunogenic composition capable of inducing an immune response that reduces the incidence of or lessens the severity of *A. suis* infection in a subject. An effective amount refers to colony forming units (CFU) per dose or logs/dose.

"Long-lasting protection" shall refer to "improved efficacy" that persists for at least 3 weeks, but more preferably at least 3 months, still more preferably at least 6 months. It is most preferred that the long lasting protection shall persist until the average age at which porcine animals are marketed for meat.

Herein, unless otherwise required by context, singular terms shall include pluralities and plural terms shall include the singular. In this application, the use of "or" means "and/or" unless stated otherwise.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Daily average temperatures among treatment groups from day 0 to day 41 of the study.

DETAILED DESCRIPTION

The invention provides methods and compositions useful for inhibiting, treating, protecting, or preventing infection by *Actinobacillus suis*. Herein are described the effectiveness of *A. suis* prototype vaccines against a heterologous challenge of various serotypes or isolates of *A. suis*. These vaccines were demonstrated to usefully stimulate immunogenic reactions in treated animals. Some vaccines stimulated reactions sufficient to be protective against *A. suis*.

The *A. suis* vaccine prototypes were comprised of different, culture fractions (e.g. whole cell, supernatant, or outer membrane protein (omp)) and a Ingelvac® APP-ALC live vaccine against *A. pleuropneumoniae* (APP). The whole cell vaccine was made from the pelleted material that resulted from a centrifugal spin of a cell culture. The cultural supernatant was made from the supernatant that resulted from the centrifugal spin, and may have included exotoxins, endotoxins, secreted or sloughed-off omps, and other cellular components that were not removed during the spin (see Example 1). The Ingelvac® APP-ALC live vaccine was included because APP encodes Apx I and II toxins that are very similar to *A. suis* toxins. It was hypothesized that the Ingelvac® APP-ALC vaccine may provide some cross protection against *A. suis*.

This efficacy study consisted of six treatment groups of weaned 3 week-old ±7 days of age pigs. Treatment group 1 (15 pigs) received a 1×2 mL intramuscular (IM) dose of a formalin-inactivated, whole cell fraction of *A. suis* on days 0 and 21 of the study, respectively. Treatment group 2 (15 pigs) received a 1×2 mL IM dose of a formalin-inactivated *A. suis* culture supernatant fraction on days 0 and 21 of the study, respectively. Treatment group 3 (15 pigs) received a 1×2 mL IM dose of an *A. suis* outer membrane protein (omp) cellular fraction on days 0 and 21 respectively. Treatment group 4 (15 pigs) received a 1×2 mL IM dose of Ingelvac® APP-ALC on days 0 and 21 respectively. Treatment group 5 (15 pigs) designated as "challenge controls" received a 1×2 mL IM dose of placebo on days 0 and 21 respectively. Treatment group 6 (10 pigs) were designated "strict controls" and did not receive vaccine or placebo treatment.

On the day of challenge (day 35) the pigs in groups 1-5 received a 6 mL dose/pig, 3 mL applied to each nostril, of *A. suis* strain ISU-8594 via intranasal (IN) inoculation containing $1\times10^{9.0}$ logs/dose. General observations were monitored throughout the study, days 0 to 41, to record the overall health of the pigs, as well as, injection site reactivity and rectal temperatures. On Day 41 of the study, all animals were euthanized, and all sections of the lung were scored for determining the percentage of lung pathology. Fresh and fixed (lungs only) samples of the lung (3 lobes with lesions, if present), liver, kidney, spleen, tonsil, and swabs of nasal turbinates, trachea, bronchi, meninges, and heart blood were collected from each animal and were cultured for bacterial isolation and histopathology (lungs only).

The A. suis fractions and placebo groups were adjuvanted with Emulsigen®-D, and a few adverse injection site reactions were noted in these groups. One pig in the supernatant group (group 2) was noted with a mild reaction at the injection site during the first vaccination event. Overall, the Emulsigen®-D in combination with the test articles did not produce any significant injection site reactions in the supernatant and omp groups. However, the whole cell group did have a few animals with abscesses present at the time of necropsy, which could have been due to the test article formulation that consisted of a concentrated whole cell stock. The administration of these vaccine prototypes (i.e. whole cell, supernatant, and omp) appeared to be well-tolerated during the time of administration. The APP-ALC group had some injection site swelling, which is consistent with the product literature that notes swelling in 11% of the vaccinated animals.

The general overall health of the pigs in each of the treatment groups was good during the pre-challenge period. Only one pig, from treatment group 4, was removed from the study during this period. This pig was removed due to a bacterial infection believed not to be associated with administration of the APP vaccine. Further observations showed one pig in the challenge control group was lame on its right leg from day 7 to day 24 of the study. This pig skewed the clinical observation results during the pre-challenge period and could have been considered an outlier and removed from the study data analysis. Also, one pig showed poor body condition in the whole cell group and died after a few days. None of the pigs in the pre-vaccination period showed signs of respiratory difficulties.

Assessment of the primary and secondary parameters were validated by significant ($p<0.05$) increases in lesion development that occurred in the challenge control group (treatment group 5) compared to the strict control group (treatment group 6). Results of this assessment validated the virulent pure culture *A. suis* challenge model in pigs. Further comparisons were made against the challenge control and not to the strict control group when comparing groups 1-4.

During the six day challenge period one pig died of acute death due to *A. suis* infection one day post-challenge in the whole cell group. Based on previous challenge studies, the intranasal route and the potency were appropriate to cause significant lesion development in the test animals and apparent fatal sudden death, as was the case for this one pig in the whole cell group.

Based on average lung lesion scores and percent with a lesion, gross lung lesion scores appeared to be most severe in the challenge group. Statistical analyses showed no statistical differences ($p<0.05$) in average lung lesion scores or percent with a lesion present when comparing groups 1 through 5. Numerically the challenge controls received overall the highest average gross lung lesion scores followed by the whole cell and omp groups, which also received relatively high scores. Lesion development was lower in the supernatant and APP groups, which received lower numerical scores compared to the other groups. All groups 1-5 had at least 50% of the pigs with a gross lesion score, and the challenge and omp groups had as much as 80% of the pigs with lesion development.

Furthermore, microscopic lung lesion analysis was based on the severity of the hallmark traits of an *A. suis* infection, i.e. bronchopneumonia, necrosis, and pleuritis. Bronchopneumonia and necrosis were more severe in the challenge control and omp groups where microscopic lesion scores were lower than in the supernatant and APP groups. The APP group showed the best signs of protection against an *A. suis* infection based on the microscopic lesion data with statistical differences ($p<0.05$) found between group 3 (omp) for necrosis and pleuritis and the group 5 (challenge) for pleuritis. Presence of bacterial colonies in all of the groups ranged from about 20% to about 46.7% with the lowest percent colonization occurring in the whole cell and APP (20.0%) groups.

The secondary parameters monitored were used to support the primary efficacy parameters (i.e., gross and microscopic (IHC) lesions) responses due to vaccine and challenge for each treatment group. Clinical observations made during the challenge period indicated that the challenge controls had an overall higher score when compared to the vaccine treatment groups 1-4, showing that the challenge controls responded to the challenge. The supernatant group did not seem to be as clinically affected. However, all groups did have some pigs that did have some respiratory issues with a cough, body condition, or behavior.

The treated groups saw an increase in average rectal temperatures, above 104° F., four hours after the first vaccination event. Temperatures for the APP and omp groups spiked at or above 104.9° F., which was the cut-off of pyrexia following four hours post vaccination, and lasted about twenty-four hours for the omp group. Temperatures in the groups were returning back to normal by day 1 or 3. For the booster event, temperatures were only taken on day 28 and not at 4 hrs or on days 1, 3, and 5 post-vaccination as with the first vaccination. During the booster period, on day 28 the APP group was statistically different ($p<0.05$) when compared to the whole cell and supernatant groups. During the challenge period, the challenge controls had an overall higher rectal temperature at both the beginning and end of the period. The whole cell group had the highest rectal temperatures during days 38 and 39. The challenge control group had the highest overall percent animals febrile ($^{10}/_{15}$) followed by the whole cell ($^{8}/_{15}$), OMP ($^{5}/_{15}$), supernatant ($^{2}/_{15}$), and APP ($^{1}/_{15}$) groups, respectively.

Bacterial isolation was highest in the lung and tonsil samples. The highest recovery of *A. suis* occurred in the challenge control group. The strict control group was negative for *A. suis* except in nasal and tonsil samples, which had 3 out of 10 and 1 out of 10 respectively. These results were recorded as a positive and not verified by BCA or other means. Possible reasons for these results could have been an inadvertent misread of the agar plate or a cross-contamination event during the processing of the swabs. Furthermore, three parameters had very low recovery rates of *A. suis* which were the spleen, meninges, and heart blood, and thus, were not included in the analysis. Overall the rate of septicemia was low due to low recovery of *A. suis* in the visceral organs and heart blood. There was also evidence that this challenge crossed the blood brain barrier in three of the animals that were severely infected. Other detected bacteria were *Bordetella*, alpha and beta streptococci.

Serology testing using a western blot procedure was performed to test for reactivity against the test article that was used to vaccinate the treatment groups. The western blots showed detectible seroconversion to the whole cell, supernatant, and omp fractions at 1:100 dilution. The APP fraction had the best reactivity and was detectable at a dilution of 1:1000, confirming that the host recognized some part of the fractions used for vaccination of each treatment group.

Overall the best protection occurred in the pigs vaccinated with the APP and supernatant prototype vaccines. Comparatively, neither the whole cell nor omp vaccines or LPS derived antigens provided much protection from *A. suis* challenge. Details of the challenge study are provided in the Examples below.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Prototype Vaccines and Challenge Treatment

A. Preparation of Vaccine Prototypes

Growth of *A. suis* (KSU-1) Cultures:

One milliliter of *A. suis* (103007-1KSU) lot #201-9,10,11 was used to inoculate 150 ml of BHI media (lot #195-121) in a 250 ml spinner. The inoculated media was placed at 37° C. at about 72 rpm for six hours. Afterwards, about 2.5 ml of the inoculated media was added to about 2500 ml fresh BHI media. This step was repeated until four batches of 2500 ml were prepared. The four batches were incubated at 37° C. overnight at about 72 rpm. Two batches were used to isolate whole cell OMP, and supernatant fractions, one batch was used to prepare a concentrated whole cell fraction, and the final batch was used for LPS extraction.

Harvesting of Cell Fractions:

Optical densities of batches were read fifteen hours after inoculation. Optical densities ranged from 0.775 to 0.815 at 600 nm. BAPs were streaked from each culture to verify that the cultures were pure for *A. suis.*

To collect the OMP and supernatant fractions, two culture batches were transferred to 500 ml centrifuge tubes, placed in a JA-10 rotor, and spun at 10K for 10 minutes. The supernatants were decanted, and the pellets were transferred into sterile 250 mL Corning centrifuge tubes. The pellets were centrifuged at about 5000 rpm in a JA-10 rotor for 10 minutes, and the remaining supernatants were removed. The pellets were pooled and placed at −80° C. until sarcosyl extraction (see below). The decanted supernatants were pooled, and filtered through 0.45 μm filters (Nalgene 0.45 SFCA) into sterile 2 L Pyrex bottles. The filtered supernatant was aliquoted into 2×850 cm RBs, 81×5 mL vials, and 4×250 mL Nalgene bottles. Filtered supernatant was stored at −20° C. until use.

To collect the concentrated (10×) whole cell pellet fraction, one culture batch was harvested as above, but the pellets were resuspended in 300 mL TSP buffer. The solution was mixed well and aliquoted into 50×2 mL vials and 4×50 mL vaccine bottles. Resuspended whole cell pellets were stored at −80° C. until use.

To prepare the LPS fraction, *A. suis* culture was harvested as described above. The pellets were resuspended in 1×PBS buffer and re-centrifuged at 10K rpm for ten minutes. Supernatants were decanted, and the pellets were resuspended in 1 L of 1×PBS buffer. An optical density reading at about 600 nm was 1.003, which is within the expected range of 0.8-1.200 for LPS extraction. The LPS fraction was aliquoted into 3×250 mL Nalgene bottles and stored at −80° C. until use. The remaining volume of LPS fraction was stored at 4° C. for LPS extraction.

KSU-1 Whole Cell Formalin-Inactivated Vaccine:

The optical density (OD) of the cell culture measured at 600 nanometer wavelength was at 0.775 at the time of harvest. In previous studies, this optical density has correlated to approximately 8.7 logs/mL based on the logarithmic estimate curve to determine logs/mL based on colony forming units (cfu). The whole cell fraction was concentrated 10× and frozen. The frozen stock was then formalin-inactivated, and diluted (54 mLs of culture into 26 mLs of 1× phosphate buffered saline (pbs), to 67.5% of the total fraction. The inactivated, diluted vaccine stock was then stored at 4° C.

The whole cell formalin-inactivated vaccine stock was removed from 4° C. for formulation. Working in a bio-safety hood 80 mLs of the material was aliquoted out into a sterile 100 mL Pyrex bottle containing a magnetic stir bar. The bottle was placed on a stir plate, and with continuous stifling, 20 mLs (20% v/v) of the adjuvant (Emulsigen®-D) was added over 1 minute. The adjuvanted prototype was then stirred for an additional 10 minutes. The material was transferred to a 100 mL vaccine bottle where it was capped and placed at 4° C. Lot nos. for the whole cell formalin-inactivated vaccine prototype were N201-110-WC-073108 (day 7) and N201-122-WC-082108 (day 21).

Sterility was verified by no growth on 5% Sheep Blood Agar Plate (BAP) after 28 hrs and 30 hrs of 37° C. aerobic incubation for day 0 and day 21 respectively. Vaccine prototype material was kept on ice prior to administration to the test animals and during the entire vaccine administration procedure.

KSU-1 Supernatant Formalin-Inactivated Vaccine:

The supernatant prototype was formulated from the 10× concentration step of the whole cell fraction preparation (see above) by collecting the supernatant and filtering it through a 0.45 micro filter. The resulting filtered supernatant was frozen. This supernatant was then formalin inactived and stored at 4° C. until formulated. The formulation step was as for the whole cell formalin-inactivated vaccine. Lot nos. for the supernatant formalin-inactivated vaccine prototype were N201-110-Supe-073108 (day 7) and N201-122-Supe-082108 (day 21).

Sterility was verified, and the vaccine prototype material was maintained prior to administration to the test animals and during the entire vaccine administration procedure as previously described.

KSU-1 OMP Fraction Vaccine:

The OMP fraction was produced from pellets prepared from a KSU-1 culture (isolate BI-103007-1KSU) and stored at −80° C. by using the following OMP sarcosyl extraction procedure. Pellets were thawed on the benchtop. The pellets were resuspended (22.5 g wet weight) with 130 mL of 10 mM HEPES balanced salt solution and aliquoted into four 50 mL conical Falcon tubes (40 mL/tube). (A 1 mL resuspended pellet sample was retained for protein quantification and analysis.) The resuspended pellets were placed in an ice bath and sonicated for 1 minute using (Large/Microtip) probe (50 mL aliquots) with a sonication pulse setting of 1 pulse/sec. The sonication was repeated three times. (A 1 mL post-sonication sample was retained.) The sonicated pellets were centrifuged at 17,000×g for 20 min in 50 mL tubes. Afterwards, the supernatants were decanted and pooled into a separate container. Pellets were stored at 4° C. until after a bicinchoninic acid assay (BCA) and then discarded.

The pooled supernatants were run in an ultra centrifuge, ~0.0128 kg/tube, at a setting of 124,000×g (30,000 rpm), 1:10 hours, 4° C., with maximum acceleration, and no brake. Supernatants were decanted, pooled with the earlier supernatant, and stored at 4° C. About 1 mL of 10 mM HEPES was added on top of each pellet in the ultra centrifuge tubes, and the pellets were incubated overnight at 4° C. to loosen the pellets from the tubes. Another 2 mL of 10 mM HEPES was added to each tube to resuspend the pellets. Each resuspended pellet solution was q.s. to 6 mL (total vol.) with 10 mM HEPES, and 6 mL of 2% Sarcosyl was added to each. Solutions were incubated for 30 min at room temperature. Afterwards, the tubes were balanced in ultra centrifuge buckets (~0.0128 kg/tube) using 2% sarcosyl and run in an ultra centrifuge at 124,000×g, 1:10 hour, 4° C., with maximum acceleration, and no brake. The supernatants were collected into a vessel, and 1 mL of 10 mM HEPES was added to each pellet. The OMP pellets were stored are 4° C. for 1 hour prior to measuring protein concentration or visualization of proteins.

Duplicate samples (1:10 dilution) were run on either a reduced MOPS 10-12% Bis-Tris SDS PAGE gel or a NuPAGE 4-12% Bis-Tris gel to visualize protein bands. Total protein concentrations of the final OMP stock were determined using the BCA and were determined prior to formulation with adjuvant. Based on the values obtained by BCA, the total mass of protein contained in the OMP extraction stock was 1.75 µg/mL. Based on this value, the potency of the formulated vaccine OMP prototype was 250 µg/dose. The resuspended, extracted OMP fraction was aliquoted into 200 µl samples, labelled, and frozen at −70° C.

Five vials containing 0.5 mLs of the extracted OMP fraction were removed from −70° C. These vials were thawed at room temperature. Working in a bio-safety hood 23.25 mLs of 1× phosphate buffered saline (pbs) and 2.35 mLs of the OMP material were aliquoted into a sterile 100 mL Pyrex bottle containing a magnetic stir bar. The bottle was placed on a stir plate, and with continuous stirring, 6.4 mLs (20% v/v) of the adjuvant (Emulsigen®-D) were added over 1 minute. The adjuvanted OMP prototype vaccine was then stirred for an additional 10 minutes. The OMP prototype vaccine was transferred to a 60 mL vaccine bottle where it was capped and placed at 4° C. Lot nos. for the OMP vaccine prototype were N201-110-OMP-073108 (day 7) and N201-122-OMP-082108 (day 21).

Sterility was verified, and the vaccine prototype material was maintained prior to administration to the test animals and during the entire vaccine administration procedure as previously described.

Ingelvac® APP-ALC Vaccine:

One bottle of APP-ALC was removed from −70° C. and thawed in luke warm water. Once thawed, a sample was removed using a 16 gauge sterile needle and placed in a vaccine bottle for potency testing. The vaccine bottle was placed at 4° C. Titrations of Ingelvac APP-ALC were performed on Days 0 and 21 for determining colony forming units (CFU) per dose. The samples were serially diluted out 10-fold and plated onto Mueller Hinton Chocolate Agar plates. Three reps were performed and allowed to incubate at 37° C. for 24 hrs before determining the CFU. Colony forming units were respectively at Day 0: 9.99 logs/dose and at Day 21: 10.2 logs/dose. Lot nos. for the Ingelvac® APP-ALC vaccine were N201-110-APP-073108 (day 0) and N201-122-APP-082108 (day 21).

Vaccine prototype material was maintained prior to administration to the test animals and during the entire vaccine administration procedure as previously described.

Placebo Vaccine

Working in a bio-safety hood, 60 mLs of 1× phosphate buffered saline (pbs) was aliquoted out into a sterile 100 mL Pyrex bottle containing a magnetic stir bar. The bottle was placed on a stir plate, and with continuous stirring, 15 mLs (20% v/v) of the adjuvant (Emulsigen®-D) was added over 1 minute. The adjuvanted prototype was then stirred for an additional 10 minutes. The material was transferred to 100 mL vaccine bottle where it was capped and placed at 4° C. The Lot no. for the placebo vaccine was N 201-109.

Sterility was verified, and the placebo prototype material was maintained prior to administration to the test animals and during the entire vaccine administration procedure as previously described.

B. Preparation of Challenge Treatment

The challenge strain used was *A. suis* Isolate ISU-8594 p5. The challenge material was produced by inoculating a 1 liter Belco spinner flask containing 800 mLs of Brain Heart Infusion Porcine (BHI-Porcine) media with 5 mLs of ISU-8594 p4. The spinner was placed into a 37° C. incubator at ~100 rpm. The culture was grown to an optical density (OD600) of 0.109—about 5 hrs and 30 minutes post inoculation. The culture was then transferred to 6×100 mL vaccine bottles containing 100 mLs total volume that were stoppered and capped. Five of the bottles were placed into a cooler containing ice packs and one bottle which served to represent the other five bottles for titrations was placed in another cooler containing ice packs. The titer of the challenge material was determined by CFU count generated from plating serial 10-fold dilutions onto 5% sheep blood agar plates. The challenge titer obtained was $1.69 \times 10^8$ cfu(s)/mL or 9.0 logs/6 mL dose. The Lot no. for the challenge material was N201-138.

Challenge material was kept on ice prior to administration to the test animals and during the entire challenge procedure.

Example 2

Vaccination of Pigs

A mixture of female and neutered male porcine animals of a commercial cross and 3 weeks ±7 days of age were obtained from Wilson Prairie View Farms. Animals were healthy with no evidence of clinical respiratory disease and negative for bacterial respiratory pathogens such as *A. pleuropneumonia, H. parasuis, S. suis, P. multocida, B. bronchiseptica, E. rhusiopathiae* and *A. suis*. While allowance was made for animals to be excluded from the study if and when health problems unrelated to vaccination or challenge became apparent, no animals were removed.

At the time of arrival to the test site, all animals received a 1 mL shot of Excenel® (a short acting antibiotic). The animals were housed at the test site until the study was terminated. The animals were ear-tagged upon arrival, and housed appropriately for species, age, size, and condition. Challenge and strict control pigs were housed together in separate pens in a separate building away from the other treatment groups. At the time of challenge, the challenge controls were moved into the same building as the treated groups. All treatment groups were housed in separate pens throughout the study.

The animals were provided with a ration that was free of antibiotics and appropriate for species, age, size, and condition of the animals. The animals were in good health and nutritional status at initiation of the study. A health examination was conducted by a clinical veterinarian according to generally accepted veterinary practice on each animal prior to inclusion in the study.

A computer random number generator (Microsoft Office Excel) was used to assign each animal a unique random number. The random number was then sorted into ascending order. Assignments occurred by allocating the experimental units across treatment groups starting with the lowest block of random numbers and assigning them to treatment groups 1 through 6. Increasing in random number, the next block of experimental units were then assigned to treatment groups and so on until all animals were assigned to a treatment group.

This efficacy study consisted of 6 treatment groups of weaned 3 week-old ±7 days of age pigs. Treatment group 1 (15 pigs) received a 1×2 mL intramuscular (IM) dose of formalin-inactivated whole cell *A. suis* on days 0 and 21 of the study, respectively. Treatment group 2 (15 pigs) received a 1×2 mL IM dose of formalin-inactivated *A. suis* culture supernatant on days 0 and 21 of the study, respectively. Treatment group 3 (15 pigs) received a 1×2 mL IM dose of *A. suis* outer membrane protein (omp) on days 0 and 21 respectively. Treatment group 4 (15 pigs) received a 1×2 mL IM dose of Ingelvac® APP-ALC on days 0 and 21 respectively. Treatment group 5 (15 pigs) designated as "challenge controls" received a 1×2 mL dose of placebo by IM route of administration on days 0 and 21 respectively. Treatment group 6 (10 pigs) were designated "strict controls" and did not receive vaccine or placebo treatment. All groups were observed for 41 days.

On Day 35 of the study, Groups 1-5 received a 6 mL dose/pig (3 mL applied to each nostril per pig) of *A. suis* strain ISU-8594 via intranasal (IN) inoculation containing $1 \times 10^{9.0}$ logs/dose. Group 6, the "strict control" group, did not receive any treatment or challenge.

Rectal temperatures were collected from all animals prior to treatment on Day 0; 4 hours post inoculation; and on 1 day(s) post inoculation (DPI), 3, 5, 7, 14, 21, 28, 34, 35, 36, 37, 38, 39, 40 and 41 DPI.

Venous whole blood (6-10 mL) was collected from each animal prior to treatment on Day 0 and weekly (Days 7, 14, 21, 28, 34 and 41) for future serological testing.

Injection sites were examined prior to treatment and at 4, 24, 48, and 72 hours post inoculation in all pigs of Groups 1-5. The injection sites were examined for swelling, hardness, and size. The data were documented. The following scoring system was used for injection site observations: swelling (0=none, 1=swelling present), appearance (0=normal, 1=hard, 2=soft, 3=abscessed, 4=draining), size (0=normal, for all others, the length by width dimensions in centimeters (i.e. length×width×diameter) were recorded).

Clinical observations were performed daily from Day 0 to Day 41 for any signs of respiratory distress including labored breathing, sneezing, coughing, altered respiratory movements, anorexia, lameness, swelling of joints, dehydration, ability to stand, paddling, moribund for 2 or more consecutive days, or death.

Animals that had severe clinical symptoms during the study were humanely euthanized and necropsied to determine the cause of death. On Day 41 of the study, all animals were euthanized and all sections of the lung were scored for determining the percentage of lung pathology. Fresh and fixed (lungs only) samples of the lung (3 lobes with lesions, if present), liver, kidney, spleen, tonsil, and swabs of nasal turbinates, trachea, bronchi, meninges, and heart blood were collected from each animal and cultured for bacterial isolation and histopathology (lungs only).

Example 3

Evaluating Efficacy of Prototype Vaccines

A. Statistical Analysis

Statistical Analysis was performed using SAS version 9.1.3 for data management and analysis. Summary statistics including mean, standard deviation, standard error, median, range, 95% confidence intervals, coefficient of variation, and frequency distributions were generated for all data where appropriate. Analyses included all pairwise comparisons between all piglet treatment groups. All tests for significance were two-tailed with a $p \leq 0.05$ level to determine differences between treatment groups.

Primary Efficacy Parameters were non-normally distributed microscopic lesion scores and gross lesion scores that were compared by Wilcoxon Two-Sample Test and Fisher's Exact Test. Secondary Efficacy Parameters were (1) clinical signs that were compared using the Wilcoxon Two-Sample Test; (2) pyrexia that was compared using the Fisher's Exact Test and ANOVA; and (3) bacterial isolation was compared using the Fisher's Exact Test.

B. Moribund Animals

Two animals were removed from the study after study initiation. Animal ID #31 (treatment group 4) was found dead on day 11 of the study. Gross examination showed that this pig was in poor condition and thin. Its lungs had red and purple discoloration, and its abdomen had purulent exudates with fibrous peritonitis. The presumptive diagnosis was HPS or a streptococcal infection. Bacteriology cultures were performed on the fresh tissue and swab samples using standard techniques accepted in the field. The recovered bacterial colonies were analyzed, and the analysis found that the pig was infected with *Arcanobacterium pyrogenes, Aeromonas hydrophilia*, and *Citrobacter freundii*. Histopathology on fixed lung samples indicated no evidence of pneumonia, necrosis, pleuritis, or bacterial colonies present.

Animal ID #32 (treatment group 1) was found dead on day 36 one day post-challenge. Gross examination showed that this pig's lungs had severe fibrinouses and fluid in the chest cavity. Its lungs had consolidation and large hemorrhagic areas. The presumptive diagnosis was acute death due to *A. suis* challenge. Bacteriology cultures were performed on the fresh tissue and swab samples. *Actinobacillus suis* was recovered in all tissue and swab samples except the spleen and trachea. Histopathology on fixed lung samples indicated evidence of severe pneumonia, necrosis, pleuritis, and bacterial colonies present.

C. General Observations

Animals were observed daily from vaccination/placebo administration to challenge (days 0 through 35) for adverse events attributed to treatment with test/control articles or other non-treatment derived health abnormalities.

General health observations for pigs in challenge control and strict control groups (groups 5 and 6) were as follows: Pig #71 (challenge control) started showing signs of lameness on its right front on day 7 and persisted to day 24 before symptoms ceased. The rest of the pigs were normal for this period of observation.

General health observations for pigs in vaccine treatment groups (groups 1-4) were as follows: Pig ID #51 (whole cell, group 1) showed poor body condition on day 1 and persisted for three days. In treatment group 4 (APP, group 4) Pig ID #31 was removed from the study as stated above. The remaining pigs in groups 1 through 4 had normal health observations.

Injection site reactions for IM-vaccinated treatment groups 1, 2, 3 and 4 were as follows: Pigs #35 (supernatant, group 2) and #10 (APP, group 4) had swelling of a 1×1 cm² area recorded on days 1, 2, and 3 of the study. No injection site evaluations were recorded for the day 21 vaccination event. Clinical observations revealed swelling in the neck in pig #10 (APP, group 4) on days 4 and 5, pig #20 (APP, group 4) on days 26 and 29, pig #40 (APP, group 4) on days 19 through 35, pig #41 (APP, group 4) on days 26 through 35, and pig #46 (APP, group 4) on days 14 through 35. All remaining animals had a normal, healthy disposition during this observation period.

At time of necropsy, pigs #69 and #75 both in treatment group 1 (whole cell) were recorded as having neck abscesses at the site of injections. No other adverse injection site recordings were reported during necropsy.

D. Primary Efficacy Parameters

1. Gross Lesions

At necropsy (day 41 of the study), the lungs were removed from each pig and examined for gross lesions. Individual lobes were scored for percent involvement, and a total score was assigned to each individual pig. Table 1 shows the average lung lesion scores for each treatment group and the number of animals with a positive score per group.

TABLE 1

Average gross lung lesion scores by treatment group and number of animals with a positive gross score within groups.

| Group | Treatment | N | Mean | Percent with Lesion Present |
|---|---|---|---|---|
| 1 | Whole Cell | 15 | 26.73 | 66.67% (10/15) |
| 2 | Supernatant | 15 | 12.68 | 60.00% (9/15) |
| 3 | OMP | 15 | 21.69 | 80.00% (12/15) |
| 4 | APP | 14 | 16.25 | 50.00% (7/14) |
| 5 | Challenge | 15 | 28.67[a] | 86.67[a] (13/15) |
| 6 | Strict | 10 | 0.00[a] | 0.00[a] (0/10) |

[a]Groups 5 vs. 6 comparisons are statistically significant different (p < 0.05, Wilcoxon Two Sample Test and Fishers Exact Test where appropriate).

Using the Wilcoxon Two-Sample Test and Fishers Exact Test on the number of positive lesions per group, statistical analyses were run to compare the means among treatment groups 5 vs. 6 and groups 1-4 vs. 5 on average gross lesion scores. Treatment group 6 (strict controls) was negative for gross lesion development (0) and the number of percent positive scores (0%). Evaluation of groups 1-5 for average lung lesion scores and percent with a lesion ranged from 12.68 to 28.67 out of a possible 100 and from 50.00% to 86.67% respectively.

Treatment group 5 (challenge), received the highest average gross lung lesion score (28.67) and percent with a lung lesion score (86.67%) compared to the other treatment groups. Treatment group 5 was significantly different ($p \leq 0.05$) from treatment group 6, when comparing average gross lung lesion scores and percent positive with a lesion. Treatment group 2 (supernatant) received the lowest lesion score (12.68), but had a percent lesion score that was the second lowest (60.00%) compared to treatment group 4 (APP) which had the lowest percent lesion score (50.00%). Comparisons of groups 4 vs. 5 for percent with a lung lesion score was almost statistically different (p=0.0502). Furthermore, treatment group comparisons for gross lesion score of groups 4 vs. 5 and groups 2 vs. 5 were not statistically different, ($p \leq 0.0840$) and ($p \leq 0.0685$) respectively. Numerically, treatment group 1 (whole cell) had the second highest average lung lesion score of 26.73 followed by the treatment group 3 (omp) with a score of 21.69. Treatment group 3 (omp) had the second highest number of percent lesions present with 80.00% followed by treatment group 1 (whole cell) with 66.67%.

2. Microscopic Lesions

Lung sections were collected, fixed, and submitted to the Iowa State Veterinary Diagnostic Laboratory for evaluation of non-specific microscopic lesion development (i.e. pneumonia, necrosis, and pleuritis) and presence of bacterial colonies. Scores were based on a nominal scale of 1 to 3 with 1 being mild, 2 being moderate, and 3 being severe. Groups were compared based on average lesion severity and presence of bacterial colonies (bugs) present within each tissue, and the frequency of positives for each group are shown in Table 2.

TABLE 2

Average microscopic lesion scores by treatment group and number of animals with a positive microscopic score within groups.

| Grp | Treatment | N | Broncho Pneumonia lesion | Necrosis | Pleuritis | Broncho Pneumonia | Necrosis | Pleuritis | Bacterial Colonies |
|---|---|---|---|---|---|---|---|---|---|
| 1 | Whole Cell | 15 | 1.07 | 0.67 | 1.67 | 53.33% (8/15) | 40.00% (6/15) | 60.00% (9/15) | 20.00% (3/15) |
| 2 | Supernatant | 15 | 0.87 | 0.8 | 1.13 | 46.67% (7/15) | 40.00% (6/15) | 46.67% (7/15) | 33.33% (5/15) |
| 3 | OMP | 15 | 1.60 | 1.47[c] | 1.60[c] | 66.67% (10/15) | 60.00% (9/15) | 66.67% (10/15) | 46.67% (7/15) |
| 4 | APP | 15 | 0.93 | 0.47[c] | 0.67[b,c] | 46.67% (7/15) | 26.67% (4/15) | 46.67% (7/15) | 20.00% (3/15) |
| 5 | Challenge | 15 | 1.27[a] | 0.93[a] | 1.93[a,b] | 66.67%[a] (10/15) | 46.67%[a] (7/15) | 66.67%[a] (10/15) | 40.00% (6/15) |
| 6 | Strict Control | 10 | 0.00[a] | 0.00[a] | 0.00[a] | 0.00%[a] (0/10) | 0.00%[a] (0/10) | 0.00%[a] (0/10) | 0.00% (0/10) |

[a]Groups 5 vs. 6 comparisons are statistically significant different (p < 0.05, Wilcoxon Two Sample Test and Fishers Exact Test where appropriate).
[b]Groups 4 vs. 5 comparisons are statistically significant different (p < 0.05, Wilcoxon Two Sample Test and Fishers Exact Test where appropriate).
[c]Groups 3 vs. 4 comparisons are statistically significant different (p < 0.05, Wilcoxon Two Sample Test and Fishers Exact Test where appropriate).

Using the Wilcoxon Two-Sample Test, statistical analyses were run to compare the means among treatment groups on average microscopic lung lesions scores. The Fisher Exact Test was also performed on the number of positive scores for the percent positive animals per group for each parameter. Statistical differences (p≤0.05) were found when comparing treatment groups 5 (challenge) vs. 6 (strict control) for bronchopneumonia, necrosis, and pleuritis lesion scores, and percent positive. The scores were zero in all parameters for treatment group 6 (strict controls) (Table 2).

The highest bronchopneumonia lesion scores (1.60) were found in treatment group 3 (omp) followed by (1.27) treatment group 5 (challenge). The lowest received score (0.87) was in group 2 (supernatant) followed by (0.93) group 4 (APP). Scores for bronchopneumonia ranged from 0.87 to 1.60. Comparing necrosis lesion scores for treatment groups 1-5 ranged from 0.47 found in group 4 (APP) to 1.47 found in group 3 (omp). Statistical differences (p≤0.05) were found when comparing treatment groups 3 vs. 4 for necrosis. Further comparisons of treatment groups 1-5 for the pleuritis parameter revealed lesion scores that ranged from 0.67 in group 4 (App) to 1.93 in group 5 (challenge). Statistical differences (p≤0.05) were found when comparing treatment groups 3 vs. 4 and 4 vs. 5 for pleuritis. Comparison of treatment groups 1 vs. 4 was very close to being statistically different (p=0.0544).

Numerical comparisons of percent positives showed that when compared to treatment groups 1, 2, 4, and 5 treatment group 3 (omp) received the highest scores for bronchopneumonia, necrosis, pleuritis, and bacterial colonies of 66.67%, 60.00%, 66.67%, and 46.67% respectively. The highest scores were shared with treatment group 5 (challenge) for bronchopneumonia and pleuritis parameters. Furthermore, comparisons of percent positives showed that when compared to the treatment groups 1, 2, 3, and 5 the lowest scores were in treatment group 4 (APP) for bronchopneumonia, necrosis, pleuritis, and bacterial colonies of 46.67%, 26.67%, 46.67%, and 20.00% respectively. Treatment group 2 (supernatant) had the same lowest scores in bronchopneumonia and pleuritis parameters as group 4, and group 2 and group 1 (whole cell) had the same frequency of bacterial colonies present. No statistical differences were found for percent positives in the parameters listed in Table 2.

E. Secondary Efficacy Parameters

Secondary parameters were used to support primary efficacy parameters in this study. Statistical analyses were performed on the following secondary parameters.

1. Clinical Observations

Observations for clinical signs were made from the day of vaccination throughout the study (days 0 through 41). Four main parameters were scored: body condition (gauntness) on a scale of 1 to 3 with 1 being normal and 3 being dead; behavior (depression); locomotion; and respiration, each on a scale of 1 to 4 with 1 being normal and 4 being dead. An average clinical score was used from all 4 parameters by which a normal, healthy animal received a score of 1 while a severely affected animal (dead) could have a maximum score of 3.75. Table 3 shows the average scores by treatment group. Using the Wilcoxon Two-Sample Test, statistical analysis was only performed to compare groups 1 through 5 on average clinical observation scores.

TABLE 3

Daily average clinical scores for pre-challenge and post-challenge periods within each treatment group.

| Grp | Treatment | Pre-Challenge Days (0-35) | Post Challenge | | | | | | Post Challenge Days (36-41) |
|-----|-----------|---------------------------|----------------|---|---|---|---|---|---|
| | | | Day 36 | Day 37 | Day 38 | Day 39 | Day 40 | Day 41 | |
| 1 | Whole Cell | 1.001$^{a,b}$ | 1.25$^b$ | 1.04 | 1.00 | 1.02 | 1.04 | 1.07 | 1.068$^a$ |
| 2 | Supernatant | 1.000$^{a,b}$ | 1.03 | 1.03 | 1.00 | 1.00$^a$ | 1.00$^a$ | 1.03$^a$ | 1.017$^a$ |
| 3 | OMP | 1.000$^{a,b}$ | 1.07$^b$ | 1.03 | 1.05 | 1.00$^a$ | 1.05 | 1.13 | 1.058$^a$ |
| 4 | APP | 1.011$^b$ | 1.00$^{a,b}$ | 1.02 | 1.00 | 1.02 | 1.04 | 1.14 | 1.036$^a$ |
| 5 | Challenge | 1.013$^a$ | 1.12$^a$ | 1.08 | 1.12 | 1.28$^a$ | 1.14$^a$ | 1.14$^a$ | 1.148$^a$ |
| *6 | Strict | 1.000 | 1.00 | 1.00 | 1.00 | 1.00 | 1.00 | 1.00 | 1.000 |

*Treatment group 6 was not included in the statistical analysis.
$^a$Groups 1-4 vs. 5 comparisons are statistically significant different (p < 0.05, Wilcoxon Two Sample Test where appropriate).
$^b$Groups 1-3 vs. 4 comparisons are statistically significant different (p < 0.05, Wilcoxon Two Sample Test where appropriate).

Comparison of the treatment groups 1-5 during the pre-challenge period revealed that during this time period compared to the treated groups 1-4 the untreated challenge controls had the highest clinical scores of 1.013. Treatment group 4 (APP) had the second highest mean clinical score of 1.011 followed by groups 1, 2 and 3 with scores of 1.001, 1.000, and 1.000 respectively. Statistical differences (p≤0.05) were found when comparing treatment groups 1-3 vs. group 5 from an overall mean score for the pre-challenge period. In addition statistical differences (p≤0.05) were found when comparing groups 1-3 vs. group 4. No statistical differences were found when comparing group 4 vs. group 5.

During the challenge period it was noted that treatment group 5 (challenge) had the highest overall score of 1.148 followed by groups 1, 3, 4, and 2 with scores of 1.068, 1.058, 1.036, and 1.017 respectively. For overall average clinical scores, statistical differences (p≤0.05) were found when comparing groups 1-4 vs. group 5. During the challenge period, treatment group 5 (challenge) had the highest scores on days 37 through 41. Treatment group 1 (whole cell) had the highest score on day 36. Furthermore, treatment group 1 (whole cell) scores fell numerically following day 36 spike from 1.25 to a range of 1.00 to 1.07. The lowest overall score was in treatment group 2 (supernatant), and it was statistical different (p≤0.05) compared to group 5 (challenge) on days 39, 40, and 41. Further comparison of group 4 (APP) showed that on day 36, one day post challenge, there was a statistical difference (p≤0.05) compared to group 5 (challenge). Also, on day 36 groups 1 and 3 were statistical different (p≤0.05) compared to group 4 (APP).

2. Rectal Temperatures

To monitor the effects of vaccination and challenge, rectal temperatures were taken at different time points throughout the study (Days 0, 0+4 hrs, 1, 3, 5, 7, 14, 21, 28, 34, 35, 36, 37, 38, 39, 40, and 41). Temperature spikes greater than (104.9° F.) were considered to be significant. The number of animals with temperatures exceeding the cut-off are listed in Table 4. Using Fisher's Exact Test and ANOVA, statistical analyses were only performed to compare pyrexia scores for groups 1 through 5.

Referring to FIG. 1 and Table 4 for the first vaccination time period of day 0 to 21, there was a general spike in rectal temperature in all treatment groups with a larger spike ≥104.9° F. at time 4 hours post vaccination in treatment groups 3 (omp) and 4 (APP) and continued to day 1 for group 3 (omp). In group 1 (whole cell) there was a decrease in temperature on day 7 to 102° F., and statistical differences were observed (p≤0.05) when comparing group 1 vs. groups 2-5 on this day. Furthermore, the treated animal temperatures in groups 1-4 were numerically less than the untreated groups 4-5 on day 7. On day 21 of the study the treated animals had numerically lower temperatures than the untreated and were found to be statistically different (p≤0.05) when comparing groups 1-4 vs. group 5.

TABLE 4

Rectal temperatures (° F.) from day 0 to day 21 (first vaccintion period).

| Grp | Treatment | Day 0 | Day 0 + 4 hrs. | Day 1 | Day 3 | Day 5 | Day 7 | Day 14 | Day 21 |
|---|---|---|---|---|---|---|---|---|---|
| 1 | Whole Cell | 103.1 | $104.1^b$ | $103.5^b$ | 103.3 | 103.5 | $102.0^{a,b}$ | $103.4^{a,b}$ | $103.7^{a,b}$ |
| 2 | Supernatant | 103.2 | $104.2^c$ | $103.6^c$ | 103.3 | 103.3 | $102.8^{a,b}$ | 103.6 | $103.3^{a,b}$ |
| 3 | OMP | 103.2 | $104.9^{a,b,c,d}$ | $104.9^{a,b,c}$ | 103.3 | 103.3 | $102.8^{a,b}$ | 103.6 | $103.5^a$ |
| 4 | APP | 103.3 | $105.1^{a,b,d}$ | $103.9^c$ | 103.2 | 103.5 | $102.9^{a,b}$ | $103.8^b$ | $103.5^a$ |
| 5 | Challenge | 103.1 | $103.8^a$ | $103.5^a$ | 103.5 | 103.6 | $103.6^a$ | $103.7^a$ | $104.1^a$ |
| 6 | Strict | 103.1 | 103.8 | 103.2 | 103.5 | 103.7 | 103.5 | 104.1 | 104.1 |

*Treatment group 6 was not included in the statistical analysis.
[a]Groups 1-4 vs. 5 comparisons are statistically significant different (p < 0.05, ANOVA Test where appropriate).
[b]Groups 1 vs. 2-4 comparisons are statistically significant different (p < 0.05, ANOVA where appropriate).
[c]Groups 2 vs. 3-4 comparisons are statistically significant different (p < 0.05, ANOVA where appropriate).
[d]Groups 3 vs. 4 comparisons are statistically significant different (p < 0.05, ANOVA where appropriate).

Referring to FIG. 1 and Table 5, for the booster time period of day 22 through day 35 it was observed that treatment group 4 (APP) had the highest numerical rectal temperature on day 28 of the study. Statistical differences were observed (p≤0.05) on day 28 when comparing treatment groups 1 and 2 vs. group 4.

TABLE 5

Rectal temperatures in degrees Fahrenheit (° F.) from day 22 to day 35 (booster period).

| Group | Treatment | Day 28 | Day 34 | Day 35 |
|---|---|---|---|---|
| 1 | Whole Cell | $103.7^a$ | 103.5 | 103.9 |
| 2 | Supernatant | $103.6^b$ | 103.7 | 104.0 |
| 3 | OMP | 103.9 | 103.6 | 103.8 |
| 4 | APP | $104.3^{a,b}$ | 103.5 | 103.7 |
| 5 | Challenge | 103.9 | 103.5 | 103.7 |
| 6 | Strict | 103.9 | 103.5 | 103.7 |

*Treatment group 6 was not included in the statistical analysis.
[a]Groups 1 vs. 2-4 comparisons are statistically significant different (p < 0.05, ANOVA where appropriate).
[b]Groups 2 vs. 3-4 comparisons are statistically significant different (p < 0.05, ANOVA where appropriate).

Referring to FIG. 1 and Table 6, for the challenge time period days 36 through day 41 it was observed that treatment group 5 (challenge) had the highest numerical rectal temperatures on days 36, 37, 40, and 41; whereas, treatment group 1 (whole cell) had the highest rectal temperatures on days 38 and 39. Furthermore, treatment group 4 (APP) had the lowest overall rectal temperatures on days 36, 37, 38, and 41. In addition treatment group 5 (challenge) had the same lowest temperature on day 38 as treatment group 4, and groups 2 and 3 had the lowest temperatures on days 39 and 40 respectively. Both groups 3 and 5 had an initial rise in temperature one day post-challenge that then fell for group 3; however, the temperature for group 5 rose again on day 40.

TABLE 6

Rectal temperatures (° F.) from day 36 to day 41 (challenge period) and number of animals with pyrexia (≥104.90° F.) in parentheses for at least one day from day of challenge to necropsy.

| Group | Treatment | Day 36 | Day 37 | Day 38 | Day 39 | Day 40 | Day 41 | % Present |
|---|---|---|---|---|---|---|---|---|
| 1 | Whole Cell | 104.0 | 104.1 | 103.9$^b$ | 104.0 | 103.7 | 103.8$^b$ | 53.33%$^b$ (8/15) |
| 2 | Supernatant | 103.7$^a$ | 103.8$^a$ | 103.7 | 103.5 | 103.9 | 103.9$^c$ | 13.33%$^{a,b}$ (2/15) |
| 3 | OMP | 104.3 | 103.9$^a$ | 103.8 | 103.8 | 103.4$^a$ | 103.8$^c$ | 33.33% (5/15) |
| 4 | APP | 103.5$^a$ | 103.6$^a$ | 103.5$^b$ | 103.7 | 103.6$^a$ | 103.1$^{a,b,c}$ | 7.14%$^{a,b}$ (1/14) |
| 5 | Challenge | 104.6$^a$ | 104.4$^a$ | 103.5 | 103.7 | 104.1$^a$ | 104.0$^a$ | 66.67%$^a$ (10/15) |
| 6 | Strict | 103.7 | 103.8 | 103.7 | 103.6 | 103.6 | 103.5 | 103.7 |

*Treatment group 6 and Spleen, Meninges, and Heart Blood were not part of the statistical analysis.
$^a$Groups 1-4 vs. 5 comparisons are statistically significant different (p < 0.05, ANOVA and Fishers Exact Test where appropriate).
$^b$Groups 1 vs. 2-4 comparisons are statistically significant different (p < 0.05, ANOVA and Fishers Exact Test where appropriate).
$^c$Groups 2-3 vs. 4 comparisons are statistically significant different (p < 0.05, ANOVA and Fishers Exact Test where appropriate).

Further evaluation of the challenge period showed that the challenge group 5 received the highest percent positive of animals that were febrile with a value of 66.67%, which was statistically different (p≤0.05) when compared to groups 2 and 4. The second highest score received was in treatment group 1 with a score of 53.33%, which was also statistically different (p≤0.05) when compared to groups 2 and 4. Groups 4 (APP) and 2 (supernatant) received the lowest scores of 7.14% and 13.33% respectively. Treatment group 3 (omp) had a score of 33.33%.

3. Bacterial Isolation

At necropsy, swabs of the nasal cavity, trachea, bronchi, meninges, and heart blood were collected for bacterial isolation. Sheep blood agar plates (5% with TSA) and MacConkey agar plates were inoculated with each swab, streaked for isolation and incubated overnight at 37° C. Blood agar plates were placed under anaerobic and aerobic conditions, and the MacConkey agar plates were placed under aerobic conditions only. In addition, chocolate agar plates were used only for culturing lung samples and incubated at 37° C. under aerobic conditions. Fresh tissue samples of the lung (3 lobes from sections containing lesions), liver, kidney, and tonsil were obtained. Swabs of each tissue were used to inoculate agar plates for bacterial isolation. Plates were incubated along with the swab samples mentioned above, and plates were observed for presence of A. suis 24 hours post incubation. Biochemical analysis was done on a random sample in each of the treatment groups to confirm the presence of A. suis. Statistical analyses were only performed to compare groups 1 through 5 on bacterial isolation scores using the Fisher's Exact Test. The spleen, meninges, and heart blood were not statistically analyzed. Tables 7a and 7b provides a summary of the bacteriology results.

TABLE 7a

Number of percent positive A. suis animals in treatment groups by bacterial isolation.

| Group | Treatment | Lung | Liver | Kidney | Tonsil | Nasal |
|---|---|---|---|---|---|---|
| 1 | Whole Cell | 40% (6/15) | 6.67% (1/15) | 6.67% (1/15) | 66.67% (10/15) | 13.33% (2/15) |
| 2 | Supernatant | 33.33% (5/15) | 0.00% (0/15) | 13.33% (2/15) | 80.00% (12/15) | 13.33% (2/15) |
| 3 | OMP | 33.33% (5/15) | 0.00% (0/15) | 0.00% (0/15) | 60.00% (9/15) | 6.67% a (1/15) |
| 4 | APP | 33.33% (5/15) | 6.67% (1/15) | 6.67% (1/15) | 60.00% (9/15) | 0.00% a (0/15) |
| 5 | Challenge | 73.33% (11/15) | 13.33% (2/15) | 20.00% (3/15) | 86.67% (13/15) | 46.67 a (7/15) |
| *6 | Strict | 0.00% (0/10) | 0.00% (0/10) | 0.00% (0/10) | 0.00% (0/10) | 20.00% (3/10) |

*Treatment group 6 and Parameters Spleen, Meninges, and Heart Blood were not part of the statistical analysis.
aGroups 1-4 vs. 5 comparisons are statistically significant different (p < 0.05, Fishers Exact Test where appropriate).

TABLE 7b

Number of percent positive A. suis animals in treatment groups by bacterial isolation.

| Group | Treatment | Trachea | Bronchi | *Spleen | *Meninges | *Heart blood |
|---|---|---|---|---|---|---|
| 1 | Whole Cell | 6.67% (1/15) | 13.33% (2/15) | 0.00% (0/15) | 6.67% (1/15) | 6.67% (1/15) |
| 2 | Supernatant | 6.67% (1/15) | 0.00% (0/15) | 0.00% (0/15) | 0.00% (0/15) | 0.00% (0/15) |
| 3 | OMP | 6.67% (1/15) | 13.33% (2/15) | 6.67% (1/15) | 0.00% (0/15) | 0.00% (0/15) |

TABLE 7b-continued

Number of percent positive *A. suis* animals
in treatment groups by bacterial isolation.

| Group | Treatment | Trachea | Bronchi | *Spleen | *Meninges | *Heart blood |
|-------|-----------|---------|---------|---------|-----------|--------------|
| 4 | APP | 20.00% (3/15) | 20.00% (3/15) | 0.00% (0/15) | 6.67% (1/15) | 0.00% (0/15) |
| 5 | Challenge | 20.00% (3/15) | 26.67% (4/15) | 6.67% (1/15) | 6.67% (1/15) | 6.67% (1/15) |
| *6 | Strict | 6.67% (1/10) | 0.00% (0/10) | 0.00% (0/10) | 0.00% (0/10) | 0.00% (0/10) |

*Treatment group 6 and Parameters Spleen, Meninges, and Heart Blood were not part of the statistical analysis.
<sup>a</sup>Groups 1-4 vs. 5 comparisons are statistically significant different (p < 0.05, Fishers Exact Test where appropriate).

The recovery of *A. suis* in each of the target areas was the highest in treatment group 5 (challenge) compared to the other groups (1-4). The highest percentage of *A. suis* recovery was found in the tonsil followed by the lung. The recovery of *A. suis* was low in the spleen, meninges, and heart blood parameters with only a maximum recovery yield of 6.67% among the treatment groups. The strict controls, group 6, had three out of ten pigs positive for *A. suis* in nasal tissue, and one pig positive for tracheal tissue. Statistical differences ($p \leq 0.05$) were found in nasal tissue when comparing groups 3 (omp) and 4 (APP) vs. group 5 (challenge).

Other common respiratory and bacterial organisms were isolated during the culturing process. *Bordetella* sp. was in high numbers in all groups as well as alpha and beta streptococcal bacteria and *Pasteurella multocida*. Other organisms isolated in very low numbers were *Arcanobacterium pyrogenes, E. coli, Staphylococcus* sp, *Enterococcous* sp, *Proteus*, blue fungii, and *Pastunella* sp.

4. Serology

Blood was drawn on study day 0, 7, 14, 21, 28, 34, and 41 of the study. Western blots were performed on pooled sera from treatment groups 1, 2, 3, and 4 on days 0 and 34 of the study to measure immunoreactivity to the fractions. Each treatment group consisted of three pooled groups, which consisted of 5 pigs from that treatment group. The western blots showed detectible seroconversion to the whole cell, supernatant, and omp fractions at 1:100 dilution, but not a 1:1000. The APP fraction had the best reactivity and was detectable at 1:1000. For all groups, no reactivity was found in the day 0 samples prior to treatment.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

Monteiro, Slavic, and Michael, 2000) J Clin Microbiol 38 (10): 3759-3762

Oliveira et al, (2007) American Association Of Swine Veterinarians, pp. 371-376.

Oliveira S. (2007) Swine respiratory bacterial pathogens: bacterial overview and vaccine trends. In: J Wiseman, M Varley, S McOrist & B Kemp (Eds), Paradigms in Pig Science (pp. 196-178). Nottingham, UK: Nottingham University Press.

Rullo, Papp-Szabo and Michael, (2006) Biochimie et biologie cellulaire 84 (2):184-90.

Simpson (1949) Measurement of diversity. Nature 163:688

Slavic, et al., (2000a) Can J Vet Res. 2000 April; 64 (2): 81-87.

Slavic, et al., (2000b) J Clin Microbiol. 2000 October; 38 (10): 3759-3762.

Versalovic et al, 1991, Nucleic Acids Research, Vol. 19, No. 24 6823-6831

What is claimed is:

1. An immunogenic composition for reducing the incidence or severity of a clinical sign associated with *Actinobacillus suis* infection in a subject, comprising
   a) a supernatant collected from one or more *A. suis* cultures grown to between 0.775 $OD_{600}$ and 0.815 $OD_{600}$; and
   b) an adjuvant,
wherein the reduction of the incidence of or the severity of a clinical sign is relative to a subject not receiving the immunogenic composition.

2. The immunogenic composition of claim 1, wherein the supernatant is essentially free from *A. suis* cells.

3. The immunogenic composition of claim 1, wherein the supernatant is inactivated.

4. The immunogenic composition of claim 3, wherein the supernatant is formalin inactivated.

5. The immunogenic composition of claim 1, wherein the adjuvant is an oil-in-water emulsion and dimethyldioctadecylammonium bromide (DDA).

6. The immunogenic composition of claim 1, wherein the subject is a porcine.

7. A method of provoking an immune response against *Actinobacillus suis* in a subject comprising administering to the subject the immunogenic composition of claim 1.

8. The method of claim 7, wherein the subject is a porcine.

9. A method of reducing the incidence of or severity of a clinical sign associated with *Actinobacillus suis* infection comprising the step of administering the immunogenic composition of claim 1 to a subject, wherein the reduction of the incidence of or the severity of a clinical sign is relative to a subject not receiving the immunogenic composition.

10. The method of claim 9, wherein the clinical sign is selected from the group consisting of meningitis, septicemia, metritis, pneumonia, crysipelas-like lesions, and abortion.

11. The method of claim 9, wherein the subject is a porcine.

12. A method of preparing the immunogenic composition of claim 1 comprising:
   a) growing an *Actinobacillus suis* culture to between 0.775 $OD_{600}$ and 0.815 $OD_{600}$;
   b) collecting a supernatant from the culture;
   c) filtering the supernatant to yield a filtrate; and
   d) mixing the filtrate with an adjuvant.

13. The method of claim 12, further comprising inactivating the supernatant.

14. The method of claim 13, wherein the supernatant is inactivated prior to mixing with adjuvant.

15. The method of claim 12, wherein the adjuvant is an oil-in-water emulsion and dimethyldioctadecylammonium bromide (DDA).

16. A kit comprising
   a) a filtered supernatant prepared by growing an *Actinobacillus suis* culture to between 0.775 $OD_{600}$ and 0.815 $OD_{600}$, collecting a supernatant of the culture, and filtering the supernatant;
   b) an adjuvant; and
   c) a container for packaging the supernatant and adjuvant.

17. The kit of claim 16, further comprising instructions for use of the kit.

18. The kit of claim 16, further comprising a means of administering the filtered supernatant to a subject.

* * * * *